United States Patent [19]
Gries et al.

[11] Patent Number: 5,746,999
[45] Date of Patent: May 5, 1998

[54] MAGNETIC PARTICLES FOR DIAGNOSTIC PURPOSES

[75] Inventors: Heinz Gries; Wolfgang Mützel; Christian Zurth; Hanns-Joachim Weinmann, all of Berlin, Germany

[73] Assignee: Schering Aktiengesellschaft, Berlin, Germany

[21] Appl. No.: 484,309

[22] Filed: Jun. 7, 1995

Related U.S. Application Data

[63] Continuation of Ser. No. 914,221, Jul. 16, 1992, abandoned, which is a continuation of Ser. No. 693,019, Apr. 30, 1991, abandoned, which is a continuation of Ser. No. 404,543, Sep. 8, 1989, abandoned, which is a continuation-in-part of Ser. No. 363,303, Jun. 7, 1989, abandoned, which is a continuation-in-part of Ser. No. 102,754, Sep. 24, 1987, abandoned, which is a continuation-in-part of Ser. No. 800,840, Nov. 22, 1985, abandoned.

[30] Foreign Application Priority Data

| Nov. 23, 1984 | [DE] | Germany | 34 43 251.5 |
| Nov. 23, 1984 | [DE] | Germany | 34 43 252.3 |
| Mar. 4, 1985 | [DE] | Germany | 35 08 000.0 |

[51] Int. Cl.⁶ ............................................. A61B 5/055
[52] U.S. Cl. ............................ 424/9.322; 424/493
[58] Field of Search ..................... 424/9.322, 646, 424/648, 493; 423/632, 633; 128/653.4, 654; 436/173; 428/549

[56] References Cited

U.S. PATENT DOCUMENTS

| 3,832,457 | 8/1974 | Sugimoto et al. | 424/4 |
| 4,001,288 | 1/1977 | Gable et al. | 260/439 R |
| 4,018,886 | 4/1977 | Guaever. | |
| 4,101,435 | 7/1978 | Hasegawa et al. | 252/62.53 |
| 4,452,773 | 6/1984 | Molday | 424/9 |
| 4,615,879 | 10/1986 | Runge et al. | 424/9 |
| 4,647,447 | 3/1987 | Gries et al. | 424/9 |
| 4,687,658 | 8/1987 | Quay | 424/9 |
| 4,719,098 | 1/1988 | Weinmann et al. | 424/9 |
| 4,731,239 | 3/1988 | Gordon | 424/9 |
| 4,770,183 | 9/1988 | Groman et al. | 424/9 |

FOREIGN PATENT DOCUMENTS

PCT 05554  12/1985  WIPO.

OTHER PUBLICATIONS

Widder, J. Pharm. Sci, 68 (1979) pp. 79–81.

Runge, Chem. Abs. 99 (1983) No. 4984K.

Ohgushi et al. "Dextran–Magnetite: a new relaxation reagent . . . "Chem. Abs. 89:51027; (1978).

Charles, R.G. et al. Chem Abs. 97(18):152528u (1982).

*Primary Examiner*—Gary E. Hollinden
*Attorney, Agent, or Firm*—Millen, White, Zelano, & Branigan, P.C.

[57] ABSTRACT

Agents containing magnetic particles are suitable for use in enhancing images in diagnostic procedures, e.g., via x-ray, ultrasound or especially NMR. Preferred particles are based on metals, e.g., iron, cobalt or nickel, double metal oxides/hydroxides or complexes thereof.

13 Claims, No Drawings

MAGNETIC PARTICLES FOR DIAGNOSTIC PURPOSES

This is a continuation, of the application Ser. No. 07/914,221 filed Jul. 16, 1992, which is a continuation of Ser. No. 07/693,019, filed Apr. 30, 1991 abandoned, which is a continuation of Ser. No. 07/404,543, filed Sep. 8, 1989 abandoned, which is a continuation-in-part of Ser. No. 07/363,303 filed Jun. 7, 1989 abandoned, which is a continuation-in-part of Ser. No. 07/102,754, filed Sep. 24, 1987 abandoned, which is a continuation-in-part of Ser. No. 06/800,840, filed Nov 22, 1985 abandoned.

BACKGROUND OF THE INVENTION

This invention relates to agents useful for diagnostic purposes containing magnetic particles comprising a magnetic double metal oxide/hydroxide or a magnetic metal and, if desired, a complexing agent. Furthermore, this invention relates to new complexes of double metal oxide/hydroxides and a complexing agent.

Complexes of magnetite ($Fe_3O_4$) with dextran or human serum albumin are described, for example, in U.S. Pat. No. 4,101,435 and 4,452,773 and in *J. Pharm. Sci.* 68, 79 (1979). In water they form stable colloidal solutions which are put to a wide range of uses because of their magnetic properties. Thus, they are suitable, inter alia, as drug carriers (above all as cytotoxic agents in the treatment of tumors), as agents for measurements in the blood stream, as markers in scanning/transmission electron microscopy, for marking and separating cells and biomolecules (e.g., an antigen from a mixture of antigens by using particles bound covalently to the corresponding antibody), as well as for use in the mechanical sector (e.g., for audio and video tapes). Furthermore, dextran magnetite has been suggested as a relaxant agent for measuring the exchange of water across erythrocyte membranes (*Biochem. and Biophys. Res. Comm.* 97, 114 (1980), and is generically predicted to be a radiopaque agent in U.S. Pat. No. 4,101,435.

Ferromagnetic zeolite particles have been used, for example, to separate mixtures of hydrocarbons (European patent application, publication No. 0130043).

Many of the magnetic fluids described hitherto are unsuitable for diagnostic uses, however, since they contain physiologically intolerable components.

SUMMARY OF THE INVENTION

Accordingly, it is an object of this invention to provide new magnetic materials useful in medical diagnoses.

Upon further study of the specification and appended claims, further objects and advantages of this invention will become apparent to those skilled in the art.

It has now been found that the agents of this invention meet the large number of preconditions, e.g., for suitability of contrast media for NMR diagnostics. (A detailed discussion of these preconditions can be found in European patent application, publication No. 71 564 and German patent application P 34 01 052.1 which are incorporated by reference herein.)

In one aspect, these objects have been achieved by providing magnetic particles, e.g., based on magnetic metals, double metal oxides/hydroxides, such materials in complexed form, e.g., treated with complexing agents, etc.

Thus, the invention relates to agents for use in diagnostics containing magnetic particles, e.g., based on iron, cobalt or nickel or on a double metal-oxide/hydroxide, and/or containing a complexing agent and/or containing a magnetic metal.

DETAILED DISCUSSION

Non-limiting examples of suitable magnetic components for use in this invention include metal particles, e.g., iron, cobalt, nickel, etc., particles, magnetic iron oxides, e.g., $Fe_2O_3$, $\gamma\text{-}Fe_2O_3$, and double oxides/double hydroxides which contain bivalent and/or trivalent iron such as ferrites of the general formula $mMO \cdot nFe_2O_3$, where M is a bivalent metal ion or a mixture of two bivalent metal ions, or, for example, a ferrite of the general formula $nFeO \cdot mM_2O_3$, where M is a trivalent metal ion, and m and n each independently is a value in the range of 1 to 6 including values other than the pure integers. Preferred are double oxides/double hydroxides which contain physiologically acceptable small amounts (e.g., 0.001–100 μmoles per kg of body weight) of the elements magnesium, zinc, iron and cobalt, and possibly also very small amounts (e.g., 0.01–1000 nmoles per kg of body weight) of manganese, nickel, copper, barium and strontium and/or, in the case of trivalent ions, chromium, lanthanum, gadolinium, europium, dysprosium, holmium, ytterbium and samarium. "Double" in this context refers to salts with a metal in oxidation state 2 and a metal in oxidation state 3. The salts are termed oxides/hydroxides since the preparation of the oxides proceeds conventionally via the hydroxides. Intermediates thus exist between oxides and hydroxides, e.g., $FeO \cdot OH$. See, Arzneimittelforschung 17, 796 (1967).

Non-limiting examples of physiologically tolerated complexing agents that are suitable include, for example, mono-, di-, oligo- and polysaccharides, proteins, mono- or polycarboxylic acids-optionally in the form of their esters or salts-and synthetic protective colloids such as polyvinyl alcohol, polysilanes, polyethylene imines or polyglutaraldehyde. Preferred are sugar, dextrans, dextrins, oleic acid, succinic acid, gelatins, globulins and albumins, e.g., human serum albumin, to which biomolecules are linked if desired. Such biomolecules include, for example, hormones, e.g., insulin, prostaglandins, steroids, etc. as well as amino acids, sugars, peptides, proteins or lipids. Suitable complexing agents are known and disclosed, e.g., in G.D. Parfitt, *"Dispersion of Powders in Liquids"*, 3rd Edition, applied Science Publishers London-N.J. 1981.

Especially preferred are conjugates with albumins, e.g., human serum albumin, staphylococcus protein A, antibodies, e.g., monoclonal antibodies and conjugates or inclusion compounds with liposomes which, for example, can be used as unilamellar or multilamellar phosphatidylcholine-cholesterol vesicles. Inorganic protective colloids, e.g., zeolites can also be used as complexing agents.

The complexing agents (stabilizers) inhibit the separation of magnetic particles and fluid. For this purpose the magnetic particles must be covered with a coating (e.g., a monolayer or more) of long-chain molecules that are oriented in space more or less perpendicularly to the particle surface. In the case of adsorption-stabilized magnetic fluids based on magnetic particles, the polar part of the stabilizer molecule is linked to the surface of the magnetic particle via electrostatic interaction. In the case of chemically stabilized magnetic fluids, the stabilizer molecules are chemically bound to the particle surface, as described, for example, in GDR Patent 160,532.

The magnetic particles used in accordance with this invention are colloidally distributed/soluble in the fluid media in which they are administered. The complexing option in essence can be conducted with any organic complexing agent which produces a physiologically compatible complexed particle and which affects the pharmacokinetics of the particles and/or their dispersibility in the fluid medium.

The shape of the particles is non-critical. Any regular (e.g., spherical, polygonal, etc.) or irregular shapes are employable. Similarly, the particle size distribution is not critical. Any conventional method for grinding solids to the particle sizes useful in this invention can be employed. See, e.g., U.S. Pat. No. 4,247,406. Typically, particle sizes are very small in order to aid in the dispersibility of the particles in the fluid media.

For use in NMR diagnostics the average size of the metal particles is generally less than 500 Å in diameter, typically 20–200 Å that the ferrites (or other oxide/ hydroxide) less than 150 Å in diameter, e.g., 10–150 Å and of the complexes 100–50,000 Å.

The agents of this invention are outstandingly suitable for improving the information value of the image obtained by nuclear magnetic reasonance tomography after enteral or parenteral application by changing the signal intensity. Moreover, they display the high effectiveness necessary to burden the body with the lowest possible amounts of contrast media and possess the good compatibility necessary to maintain the noninvasive character of the examination.

Furthermore, when iron functions as the carrier of the magnetic properties, i.e., a physiologically harmless element that is even essential for the human organism, this is especially favorable. Since, surprisingly, the effective dosage is extraordinarily low compared with all previously known contrast media, there is a very wide margin of safety for use of the agents of this invention (e.g., the complexes) in vivo.

The good colloidal solubility in water of the media of this invention makes it possible to prepare highly concentrated solutions to keep the volumetric load on the circulatory system within acceptable limits and balance out the dilution caused by body fluids. Furthermore, the agents in accordance with this invention display not only high stability in vitro but also surprisingly high stability in vivo.

A special advantage of the agents of this invention is the fact that the signal intensity of tissue, organs and organ systems can be greatly advantageously altered in the nuclear magnetic resonance tomogram due to the specific pharmacokinetic properties of the agents. For the first time, well tolerated contrast media are available, inter alia, for the visualization of tumors of the liver and spleen. Tumor and infraction diagnostics can be improved by binding the ferromagnetic material to biomolecules such as monoclonal antibodies specific for tumorassociated antigens or antimyosin. Non-limiting examples of monoclonal antibodies which can be used for conjugation include, especially, those that are principally directed at antigens found in the cell membrane. For example, suitable for the visualization of tumors are monoclonal antibodies per se, and/or their fragments $(F(ab)_2)$, which are directed, for example, at the carcinoembryonal antigen (CEA), human choriogonadotrophin ($\beta$-hCG) or other antigens found in tumors such as glycoproteins. Antimyosin, antiinsulin and antifibrin antibodies and/or fragments, inter alia, are also suitable.

Conjugates or inclusion compounds with liposomes are suitable for liver examinations. NMR diagnostics in the gastrointestinal tract are improved by enteral application of the agents in accordance with the invention, better differentiation of intestinal sections being achieved, for example, in the case of pancreas examinations. Special microsuspensions of only slightly dissociating barium ferrites are also excellently suitable as x-ray contrast media, especially for enteral application for diagnosis of the gastrointestinal tract. Those agents of this invention which are useful in x-ray diagnostics contain elements known to have useful x-ray cross-sections, e.g., barium, lanthanum, gadolinium, europium, dysprosium, holmium, ytterbium, samarium, etc.

The agents of this invention can be utilized in conjunction with x-ray diagnoses in accordance with fully conventional principles and procedures, e.g., as described in R. C. Weast (editor) "Handbook of Chemistry and Physics", 51st edition; The Chemical Rubber Co. Cleveland/Ohio 1970 p. E-195-E-196; and R. Barke "Ronetgenkontrastmittel", G. Thieme, Leipzig 1970; P. Thurn, E. Buecheler "Einfuehrung in die Rontgendiagnostik", G. Thieme, Stuttgart/N.Y. , 5, Auflage 1977, which disclosures are incorporated by reference herein.

Since the acoustic impedance of the agents in accordance with the invention is higher than that of body fluids and tissues, they are also suitable as contrast media for ultrasonic diagnostics.

The agents of this invention can be utilized in conjunction with x-ray diagnoses in accordance with fully conventional principles and procedures, e.g., as described in J. I. Haft "Clinical Echocardiography", Futura, Mount Kisco, N.Y. 1978; E. Koehler "Klinische Echokardiographie", Enke, Stuttgart, 1979; and G. Stefan "Echokardiographie", Thieme, Stuttgart/N.Y. 1981, which disclosures are incorporated by reference herein.

Microsuspensions of the double metal-oxide/hydroxide complexes are prepared in the way generally known by mixing aqueous solutions of the corresponding bivalent and trivalent metal salts, e.g., the halides. This is then mixed with alkali-metal hydroxides, e.g., ammonium or sodium hydroxide and/or alkali-metal carbonates, e.g., sodium carbonate, in order to raise the pH and produce the metal oxides and/or metal hydroxides in the form of extremely fine particles to which the complexing agent binds. By, for example, centrifuging and/or, for example, gel filtration chromatography and/or dialysis, it is possible to separate and purify the desired complexes.

In another method of preparation, the finely ground double oxide and/or metal is conventionally treated with the protective colloid (cf. *J. Pharm. Sci.* 68, 79, (1979)). The biomolecules can be bound conventionally, e.g., by methods such as those described, for example, in *Rev. roum. Morphol. Embryol, Physiol., Physiologie* 1981, 18, 241 and *J. Pharm. Sci.* 68, 79 1979). Zeolite-containing particles can, for example, be prepared in accordance with the details of European patent application publication No. 130043. Magnetic, silanized particles can, for example, be prepared in accordance with the details of European patent application publication No. 125995. The techniques of U.S. Pat. Nos. 4,101,435 and 4,452,773 can also be used in forming the complexes of this invention. All of the references cited above are incorporated by reference herein entirely.

The diagnostic agents of this invention can likewise be prepared in the way generally known by suspending the particles of this invention in an aqueous medium, optionally with addition of additives customary in galenicals, and subsequently sterilizing the suspension if desired. Non-limiting examples of suitable additives include, for example, physiologically biocompatible, (e.g., tromethamine) or, if necessary, electrolytes such as sodium chloride or, if necessary, antioxidants such as ascorbic acid, etc.

If suspensions of the agents of this invention are desired in water or a physiological saline solution for enteral application or other purposes, they can be mixed with one or more adjuvants customary in galenicals (e.g., methyl cellulose, lactose, mannite) and/or surfactants (e.g., lecithins, Tweens $^{(R)}$, Myrj$^{(R)}$) and/or aromatic substances for flavoring (e.g., ethereal oils).

Conventional excipients are pharmaceutically acceptable organic or inorganic carrier substances suitable for parenteral, enteral or topical application which do not deleteriously react with the agents. Suitable pharmaceutically acceptable adjuvants include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oil or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed.

The agents containing uncomplexed, magnetic particles are preferably used in enteral application, e.g., orally.

The agents of this invention generally contain from 1 µmole to 1 mole, preferably 0.1 to 100 mmoles of magnetic metal per liter and are usually dosed in amounts of 0.001 to 100 µmoles, preferably 0.1 to 10 µmoles of magnetic metal per kilogram of body weight. They are administrable enterally and parenterally to mammals, including humans. Typically, NMR measurement is begun about 5 minutes after administration.

The agents can be administered for NMR diagnoses analogously to the details disclosed iN U.S. application Ser. No. 573,184 and its parent Ser. No. 401,594, filed on Jan. 23, 1984 and Jul. 26, 1982, respectively, and corresponding to EP-A-0071564 and German Patent Application P 34 01 052.1.

Excluded from certain limited aspects of this invention can be iron oxide-dextran complexes, iron oxide- or ferrite-antibody complexes, nickel-antibody or protein complexes, iron oxide-albumin complexes and/or $Fe_3O_4$-polysaccharide complexes, e.g., those with dextran.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

A solution of 100 g of glucose in 824 ml of water is mixed with 140 ml of a 1-molar ferric chloride solution and with 70 ml of a 1-molar ferrous chloride solution so that an iron content of 11.71 g results. The mixture is adjusted to pH 2.4 at room temperature by adding drop by drop a 20% aqueous sodium carbonate solution by weight. After the development of gas finishes, 45 ml of 10-normal caustic soda is added, and the mixture is heated for reflux for 30 minutes. After cooling to room temperature the pH is raised to 6.2 by the addition of 6-normal hydrochloric acid,and the complex is then precipitated by adding 2 liters of ethanol while stirring. The preparation is centrifuged, the residue dissolved in water and foreign ions removed by dialysis. The purified solution is concentrated, filtered and lyophilized in a vacuum. The desired glucose-magnetite complex is obtained in the form of a brown powder.

EXAMPLE 2

80 g of dextrin (polymaltose, basal viscosity 0.05°/25° C.) are dissolved in 180 ml of water at 70° C. After having cooled to room temperature the solution is stirred into a mixture of 70 ml of 1-molar ferric chloride solution and 35 ml of a 1-molar ferrous chloride solution. The pH of the mixture is then adjusted to 1.7 by adding drop by drop a 20% aqueous sodium carbonate solution by weight. After the development of gas has finished, a pH of 11.0 is adjusted by adding 10N caustic soda drop by drop, the mixture being heated for reflux for 30 minutes. After cooling to room temperature the pH is adjusted to 6.2 by the addition of 6N hydrochloric acid. The complex is precipitated by the addition of 500 ml of ethanol and centrifuged, the residue being dissolved in water and foreign ions removed in dialysis. The colloidal solution is lyophilized after filtration. The desired dextrin-magnetite complex is obtained in the form of a black powder.

EXAMPLE 3

A solution of 2.5 g of human serum albumin in 10 ml of water is mixed with 720 g of ferrous chromite, $FeO \cdot Cr_2O_3$, in the form of particles with a diameter of 10–20 nm. The suspension is added to 600 ml of cottonseed oil and the emulsion homogenized by ultrasonic treatment (100 W 1 min. at 4° C.). The emulsion is then poured drop by drop with intensive stirring into 2 liters of hot cottonseed oil at a temperature of 120° C. After being kept at 120° C. for another 10 minutes, the substance is cooled to room temperature,and the microparticles obtained are washed with the help of methyl tert-butyl ether to remove the oil. After 24 hours of drying at 4° C. in the dark the desired human serum albumin/ferrous chromite complex is obtained in the form of a deep-black powder.

EXAMPLE 4

112 mg of dextrin-magnetite complex (example 2) are poured into 20 ml of a 0.9% saline solution. The colloidal solution which is pasteurized at 100° C. for 15 minutes is used for parenteral application.

EXAMPLE 5

A granulate made of 12 mg of dextrin-magnetite complex (example 2), 2.42 g of tromethamine, 45 g of mannite and 10 g of Tylose stirred into 1000 ml of distilled water, is used for enteral application.

EXAMPLE 6

150 mg of glucose-magnetite complex (example 1) are stirred into 25 ml of 0.9% saline solution. This is filled in ampoules which are heat-sterilized.

EXAMPLE 7

A granulate made of 50 mg of glucose-magnetite complex (example 1), 3.00 g of tromethamine, 50 mg of mannite and 10 g of Tylose are stirred into 1000 ml of distilled water and filled in bottles for enteral application.

EXAMPLE 8

A granulate made of 20 mg of albumin/ferrous-chromite complex (example 3), 1.8 g of tromethamine, 50 g of mannite and 8 g of Tylose are stirred into 750 ml of distilled water and used for enteral application.

EXAMPLE 9

A solution containing 250 mg of human serum albumin dissolved in 0.75 ml of water is mixed with 65 mg of zinc ferrite, $ZnFe_2O_4$, in the form of particles with a particle size of 10–20 nm in diameter. The suspension is poured into 20 ml of cottonseed oil, and the emulsion formed is homogenized by ultrasonic treatment (100 W, 1 min at 4° C.). The cooled homogeneous emulsion is poured with intensive stirring into 10 ml of hot cottonseed oil having a temperature of approx. 120° C. The mixture is stirred for another 10 min at 120° C., cooled to room temperature and the microparticles cleaned of oil with the help of methyl tert-butyl ether. After drying for 24 hours in a vacuum in the dark at 4° C. the desired complex of human serum albumin and zinc ferrite is obtained in the form of microparticles with a diameter of 500±100 nm.

EXAMPLE 10

A suspension of 31 mg of human serum albumin, 10 mg of magnetite, $Fe_3O_4$, and 6 mg of protein A (Pharmacia, Freiburg) in 0.12 ml of water is homogenized with 20 ml of cottonseed oil in an ultrasonic bath (100 W, 1 min at 4° C.). The homogenate is then poured with intensive stirring into 15 ml of hot cottonseed oil at a temperature of approx. 120° C. The mixture is stirred for another 10 min at 120° C., cooled to room temperature and the microparticles cleaned of oil with the help of methyl tert-butyl ether (15 min of centrifuging respectively at 2000×g). After drying for 24 hours in a vacuum in the dark at 4° C. the desired conjugate of human serum albumin, magnetite and protein A is obtained in the form of microparticles with a diameter of 200±80 nm. 0.5 mg of the conjugate are incubated with 500 µg of anti-CEA in 1 ml of 0.01-molar phosphate buffer at pH 8 and 37° C. for 30 minutes. The microparticles are then washed three times with the buffer solution and freezedried after centrifuging. The binding capacity amounts to 80±3 µg/mg of antibodies/microparticles. The conjugate is used in physiological saline solution for parenteral application. The corresponding antibody conjugate for parenteral application is obtained in analogous fashion by incubating the conjugate of human serum albumin, magnetite and protein A with antimyosin.

EXAMPLE 11

A solution of 3.3 g of potassium hydroxide in 12 ml of water is added to a solution of 2 g of dextran-magnetite (Meito Sangyo Co. Ltd.) in 30 ml of water. The mixture is stirred for 10 min., cooled to 5° C. and mixed with a solution of 1.5 g of 2-bromoethylamine in 1.8 ml of water. The mixture is cooled and stirred for two hours, and then brought to room temperature overnight. 2.5 g of glutaraldehyde are added at pH 6.8 and the mixture is kept at room temperature for 18 hours. The mixture is concentrated after filtration through activated charcoal, and the polymer product is isolated by precipitation with acetone. The isolated product is washed with acetone and dried in a vacuum. 2 mg of the derivative dextranmagnetite is added to 20 µl of a solution containing 0.3 mg of anti-CEA in 0.05-molar sodium bicarbonate buffer (pH 7–8). After several hours of incubation time the solution obtained is dialyzed with 0.3-molar sodium phosphate buffer and then purified by way of a Sephadex G 25 column. The desired antibody conjugate, which is used for parenteral application, is isolated by freezedrying.

The corresponding conjugate of dextran, magnetite and antimyosin is obtained in analogous fashion.

EXAMPLE 12

A granulate made of 50 mg of a zeolite-Y-magnetite complex(prepared in accordance with Europ. Pat. Application 0130 043), 3 g of tromethamine, 30 g of mannite and 15 g of Tylose are stirred into 1000 ml of water for injection and filled in bottles for enteral application.

EXAMPLE 13

150 mg of human serum albumin/zinc ferrite complex (example 9) are suspended in 25 ml of 0.9% saline solution and filled in ampoules which then are pasteurized.

EXAMPLE 14

A granulate made of 1000 mg of iron-zeolite-Y complex (prepared in accordance with European patent application 0130043), 5 g of tromethamine, 300 g of mannite and 100 g of Tylose are suspended in 20 l of water for injection and filled in bottles for oral application.

EXAMPLE 15

A mixture of lipids containing 75 mole-% egg-phosphatidylcholine and 25 mole-% cholesterol is prepared in the form of a dry substance in accordance with the process described in Proc. Natl. Acad. Sci. U.S. Pat. No. 75, 4194. 500 mg thereof are dissolved in 30 ml of diethyl ether and mixed drop by drop in an ultrasonic bath with 3 ml of a dextran-magnetite colloid diluted in a ratio of 1:2 with 0.9% saline solution. The ultrasonic treatment continues for another 10 minutes, the mixture being gently concentrated in a Rotavapor. The gelantinous residue is suspended in a 0.125-molar saline solution, and nonencapsulated portions are removed at 4° C. by repeated centrifuging (20000 g/20 min). The liposomes treated in this way are freeze-dried in a multivial. The preparation is used for intravascular application in the form of a colloidal dispersion in physiological saline solution.

EXAMPLE 16

112 mg of dextran-magnetite complex (obtained from Meito Sangyo, Japan) are poured into 20 ml of a 0.9% saline solution with stirring. The colloidal solution obtained is filled in ampoules and heat-sterilized.

EXAMPLE 17

A granulate made from 12 mg of dextran-magnetite (purchased from Meito Sangyo, Japan), 2.42 g of tromethamine, 45 g of mannite and 10 g of Tylose stirred into 1000 ml of distilled water is used for enteral application.

EXAMPLE 18

40 ml of a 1-molar ferric chloride solution are mixed with 20 ml of a 1-molar zinc chloride solution and heated to 80°

C. The hot solution is poured into a solution of 6.8 g of sodium hydroxide in 28 ml of water with intensive stirring. The mixture is refluxed for 24 hours, the suspension centrifuged after cooling to room temperature, the residue suspended in 100 ml of water and the suspension adjusted to pH 1.4 with concentrated hydrochloric acid. 18 g of dextran T 10 (Pharmacia) are dissolved in 100 ml of water and heated for reflux for one hour after addition of 1.8 ml of 40% caustic soda. After cooling to room temperature the neutral solution is mixed with 1000 ml of methanol. After standing overnight the aqueous methanol is decanted and the residue dissolved in 100 ml of water. The zinc ferrite suspension is added to this solution and the mixture heated for reflux for 40 minutes with intensive stirring. After cooling the colloidal solution is neutralized and the ions removed by dialysis. After lyophilization the dextran $ZnO \cdot Fe_2O_3$ complex is obtained in the form of a brown powder. A dextran/barium ferrite complex is obtained in an analogous manner in the form of a brown powder if a 1-molar barium chloride solution is used.

EXAMPLE 19

The dextran and zinc ferrite complex obtained in example 18 is filled in multivials. After the addition of physiological saline solution it is heated to 120° C. for 20 minutes. A ready-to-use, sterilized, colloidal solution for injection is obtained.

EXAMPLE 20

A homogenous mixture is made of 1000 g of barium ferrite with an average grain size of 1 μm, prepared in accordance with example 18 20 g of Sorbit 20 g of sodium citrate 5 g of Tylose 250 g of the mixture are stirred with 80 ml of water and serve as an x-ray contrast medium for enteral application.

EXAMPLE 21

40 ml of a 1-molar ferric chloride solution are mixed with 20 ml of a 1-molar ferrous chloride solution and heated to 80° C. The hot solution is poured into a solution of 6.8 g of sodium hydroxide in 28 ml of water accompanied by intensive stirring. The mixture is heated for reflux for 24 hours and neutralized by the addition of concentrated hydrochloric acid. A mixture of 8 g of oleic acid, 10 ml of 3 N caustic soda and 50 ml of water are heated to 60° C. until the sodium oleate has gone into solution. The solution is then poured into the magnetite microsuspension and kept at 90° C. for 30 minutes with intensive stirring. After cooling to room temperature a pH of 7.2 is adjusted and the coarse particles separated by centrifuging, which produces a colloidal solution after dialysis that contains 520 mg of iron per ml and is diluted with physiological saline solution for use as required, filled in ampoules and heat-sterilized. A colloidal solution of the corresponding zinc ferrite complex is obtained in analogous fashion by using a 1-molar solution of zinc chloride instead of the ferrous chloride solution, and a colloidal solution of the corresponding barium ferrite complex is obtained by using a 1-molar solution of barium chloride.

EXAMPLE 22

A solution of 0.5 mg of immunoglobulin G in 3 ml of water, the carbohydrate part of which has been partially oxidized in the way described in J. Biol. Chem. 234:445–48, is added to a microsuspension of 50 mg of aminopropyl-silanized magnetite particles prepared in accordance with European patent application publication No. 125995. The mixture is rendered alkaline by the addition of a buffer solution, incubated for 3 hours and then mixed with sodium borohydride. The solution is purified by gel filtration chromotography, and the protein conjugate is isolated by lyophilization in the form of a brown powder. Resuspension in a physiological saline solution supplies, after sterile filtration, the desired diagnostic agent for parenteral application. The corresponding solutions of magnetite-protein conjugate are obtained in analogous fashion with monoclonal antibodies such as antimyosin.

EXAMPLE 23

120 mg of polyethleneimine-magnetite complex, prepared in accordance with U.S. Pat. No. 4,267,234 are stirred into 20 ml of 0.9% saline solution. The colloidal solution obtained is filled in ampoules and heat-sterilized.

EXAMPLE 24

120 mg of aminopropyl-silanized magnetite particles, prepared in the way described in European patent application publication No. 125 995, are stirred into 20 ml of 0.9% saline solution. The colloidal solution obtained is filled in ampoules heat-sterilized.

EXAMPLE 25

910 mg of dextran T 10 (Pharmacia) are dissolved in 40 ml of water. The pH is adjusted to pH 11 by the addition of 1-normal caustic soda, and a solution of 295 mg of bromine cyanide in 10 ml of water is dripped in while maintaining a constant pH value. The preparation is stirred for 30 minutes, and 0.3 ml of a 6-millimolar hydrazine hydrate solution are then added. The pH is adjusted to pH 8.5 by the addition of 1-normal hydrochloric acid, and the mixture is stirred overnight at room temperature. The solution is freeze-dried after exhaustive dialysis. The dextran activated with hydrazine groups that is obtained as a white powder is used in the form of an aqueous solution as a stabilizer for magnetite particles analogous to example 2, the subsequent binding to proteins taking place analogous to example 22.

EXAMPLE 26

1080 mg of dextran M 8 (Pharmacia) are dissolved in 5 ml of a 10-percent saline solution by weight and mixed one after another with 283 mg of hyd,razine mono-chloride and 1257 mg of sodium cyanoborohydride. The preparation is maintained at 100° C. for 36 hours, and the cooled solution is then poured into 25 ml of methanol. The precipitate is sucked off and dried. The yellowish, crystalline product obtained is dissolved in water and used as a stabilizer for magnetite particles analogous to example 2; the stabilized particles are bound analogous to example 22.

EXAMPLE 27

20 ml of colloidal dextran-magnetite solution (Meito Sangyo) are diluted to 200 ml with 1-percent saline solution by weight. 60 ml of this solution are adjusted to pH 11 by adding 1-normal caustic soda and gradually mixed with 292 mg of bromine cyanide, the pH being kept constant. After the addition of 0.2 ml of hydrazine hydrate solution a pH of 8.5 is adjusted with 1-normal hydrochloric acid, and the mixture is stirred overnight. The solution is dialyzed and the dextran-magnetite activated by hydrazine groups and contained therein is bound to glycoproteins containing aldehyde groups analogous to example 22.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method comprising enhancing contrast of an MR image, by administering an effective amount of physiologically compatible alkali-pretreated polysaccharide-magnetite in particulate form.

2. A method according to claim 1, wherein the magnetite is less than 500 Å in diameter.

3. A method according to claim 1, wherein the magnetite is superparamagnetic.

4. A method according to claim 1, wherein ferric ions and ferrous ions are co-precipitated to produce magnetite in the presence of polysaccharide.

5. A method comprising enhancing contrast of an MR image, by administering an effective amount of physiologically compatible alkali-pretreated dextran-magnetite in particulate form.

6. A method according to claim 5, wherein the magnetite is less than 500 Å in diameter.

7. A method according to claim 5, wherein the magnetite is superparamagnetic.

8. A method according to claim 5, wherein ferric ions and ferrous ions are co-precipitated to produce magnetite in the presence of dextran.

9. A method comprising enhancing contrast of an MR image, by administering an effective amount of physiologically compatible dextran-magnetite in particulate form, wherein said dextran is treated with alkali prior to complexing with magnetite.

10. A method according to claim 9, wherein the magnetite is less than 500 A in diameter.

11. A method according to claim 9, wherein ferric ions and ferrous ions are co-precipitated to produce magnetite in the presence of dextran.

12. A method comprising enhancing contrast of an MR image, by administering an effective amount of physiologically compatible superparamagnetic dextran-magnetite in particulate form, wherein said dextran is treated with alkali prior to complexing with magnetite.

13. A method according to claim 12, wherein ferric ions and ferrous ions are co-precipitated to produce magnetite in the presence of dextran.

* * * * *